(12) United States Patent
Kight et al.

(10) Patent No.: US 11,191,677 B2
(45) Date of Patent: Dec. 7, 2021

(54) TAMPON INSERTION DEVICE

(71) Applicant: TINA Healthcare Corporation, Atlanta, GA (US)

(72) Inventors: Alison Marie Kight, Menlo Park, CA (US); Lovic Port Ryals, Atlanta, GA (US); Sarah Bush, Los Angeles, CA (US)

(73) Assignee: TINA HOLDINGS, LLC, Atlanta, GA (US)

( * ) Notice: Subject to any disclaimer, the term of this patent is extended or adjusted under 35 U.S.C. 154(b) by 372 days.

(21) Appl. No.: 16/416,216

(22) Filed: May 18, 2019

(65) Prior Publication Data

US 2019/0350767 A1 Nov. 21, 2019

Related U.S. Application Data

(60) Provisional application No. 62/673,748, filed on May 18, 2018.

(51) Int. Cl.
*A61F 13/26* (2006.01)
*A61F 13/551* (2006.01)

(52) U.S. Cl.
CPC ...... *A61F 13/266* (2013.01); *A61F 13/55185* (2013.01)

(58) Field of Classification Search
CPC .............................................. A61F 13/26–266
See application file for complete search history.

(56) References Cited

U.S. PATENT DOCUMENTS

| 6,019,745 | A  | * | 2/2000  | Gray ................... A61M 5/1456 604/131 |
| 2001/0041869 | A1 | * | 11/2001 | Causey, III ......... A61M 5/1456 604/152 |
| 2009/0247928 | A1 | * | 10/2009 | Bartning ................. A61F 2/005 604/15 |
| 2011/0105830 | A1 | * | 5/2011  | Hou .................... A61F 13/2097 600/30 |

FOREIGN PATENT DOCUMENTS

WO    WO-2008090667 A1 * 7/2008 ......... A61F 13/2051

\* cited by examiner

*Primary Examiner* — Susan S Su
(74) *Attorney, Agent, or Firm* — Porter Wright Morris & Arthur LLP

(57) ABSTRACT

A tampon insertion device for inserting a tampon from a tampon applicator into a vaginal canal. The devices includes a hollow casing having an open distal end, a proximal end, a top wall extending between the proximal and distal ends, an open bottom opposing the top wall, and a clamp portion located at the distal end of the casing. The device further includes a plunger actuator located in the interior of the casing for linear movement therein, and a handle slidably positioned external to the casing and connected to the actuator such that linear sliding movement of the handle with respect to the casing causes a corresponding linear movement of the actuator within the casing. A method of inserting a tampon is also provided.

17 Claims, 15 Drawing Sheets

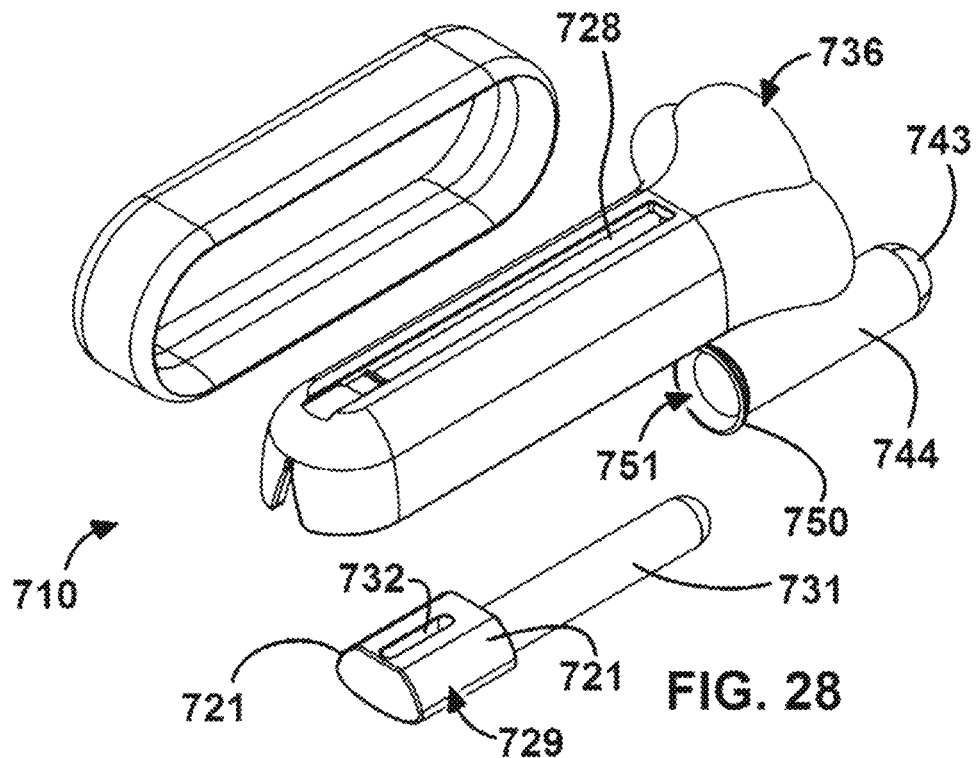
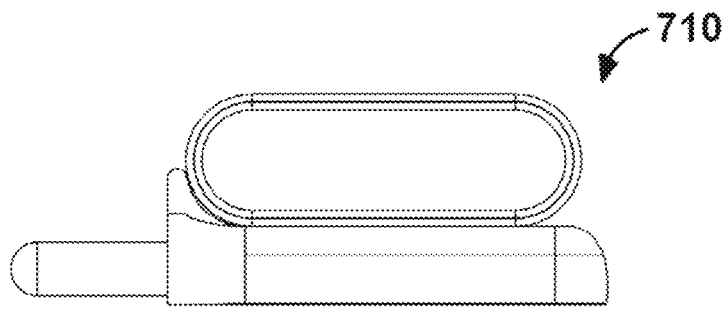
FIG. 29
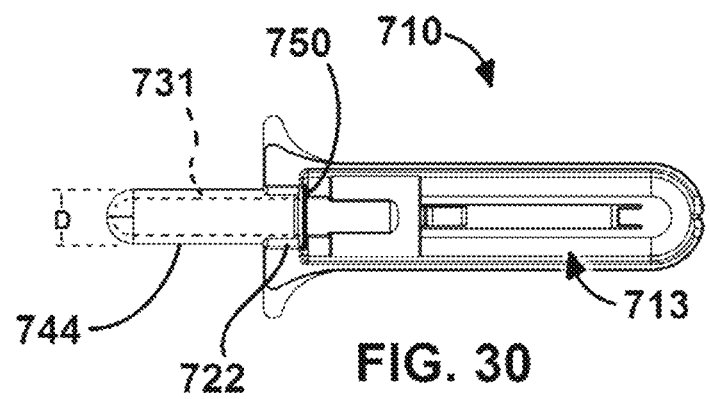
FIG. 30

TAMPON INSERTION DEVICE

CROSS REFERENCE TO RELATED APPLICATIONS

This application claims priority to U.S. Provisional Patent Application No. 62/673,748, filed on May 18, 2018, entitled "Tampon Insertion Aid." The entire disclosure of the foregoing provisional patent application is incorporated by reference herein.

BACKGROUND

Tampons are the most commonly used feminine hygiene product because they are discreet and comfortable. As opposed to bulky sanitary napkins, tampons provide a sense of cleanliness, discretion, and comfort during menstruation. Current tampons and tampon applicators require independent finger strength and dexterity for proper insertion. The user must pinch the applicator between two fingers, use forces to navigate the applicator into the vagina, maintain the original pinch force while depressing the plunger to extrude the tampon into the body, use a dexterous pinch grip again to remove the applicator from the body, and then grasp and exert tension on the external string in order to remove the tampon from the body.

In particular, a conventional tampon/applicator assembly (40) is seen in FIGS. 7 and 9 herein. The tampon/applicator assembly (40) comprises a tampon (42) (see FIG. 9) housed inside a hollow applicator barrel (44). A plunger (46) extends proximally away from the barrel (44), with the distal end (48) of the plunger (46) located inside the barrel (44), abutting against the proximal end of the tampon (42) (see FIG. 9). To insert the tampon, the user must pinch the grip portion (50) of the applicator barrel (44), insert the portion of the barrel (44) distal to the grip portion (50) into her vaginal canal (while still pinching the grip portion), and then push the plunger (46) distally into the barrel (while still pinching the grip portion) such that the tampon is expelled from the distal tip of the barrel (44) into her vaginal canal. The grip portion (50) must still be pinched by the user in order to remove the applicator barrel (44) and plunger (46) from her vaginal canal, leaving the tampon (42) in place.

This concentric cylinder tampon/applicator design actuated by dextrous hand motion originated in 1933, see U.S. Pat. No. 1,926,900 (Catamenial device), and is still the predominant tampon insertion mechanism for tampon applicators used today. Current tampons fail to accommodate women with limited finger strength and/or dexterity.

While a variety of devices and techniques may exist for inserting tampons, it is believed that no one prior to the inventors has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIG. 21A depicts an enlarged view of the indicated portion of FIG. 21.

FIG. 28 depicts an exploded rear view of the embodiment of FIG. 26.

FIG. 29 depicts a side view of the embodiment of FIG. 26, with the handle advanced distally for expelling a tampon from the barrel.

FIG. 30 depicts a bottom view of the embodiment of FIG. 29, with the location of the plunger inside the barrel also depicted in broken line.

Figure 1:
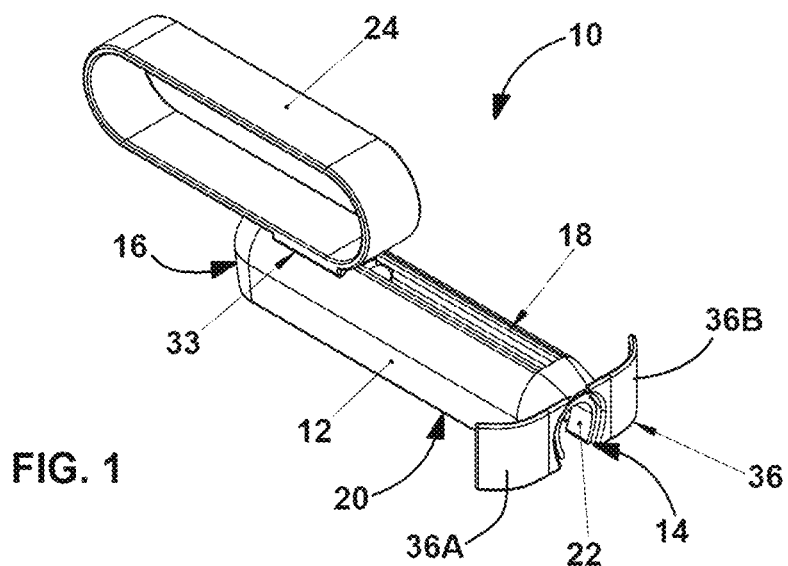
FIG. 1 depicts an orthogonal view of one embodiment of a tampon insertion device, in the ready position primed for receiving a tampon/applicator assembly therein.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

Embodiments of the present disclosure provide an apparatus for inserting tampons, particularly an apparatus that facilitates tampon insertion without requiring independent finger strength or mobility. More particularly, the present disclosure provides an apparatus for inserting tampons without requiring independent finger strength or mobility by use of a handle connected to an actuator that facilitates the dispensing a tampon from its applicator as the handle is slid linearly along the casing of the apparatus (e.g., along a linear rail on the top of the casing).

The present disclosure is centered around an innovative mechanism for facilitating tampon insertion without requiring finger strength or dexterity. Unlike conventional tampon insertion, embodiments of the present disclosure rely on increased actuating handle accessibility and less on finger strength and dexterity. As a result, individuals who have reduced finger strength and/or dexterity are better able to accomplish tampon insertion without (or with minimal) assistance.

Some embodiments of the present disclosure provide a reusable accessory that clips onto a conventional tampon/applicator assembly and allows the user to insert the cotton tampon from its applicator into the body using arm motion, without requiring finger strength or dexterity. In one particular embodiment, the device has a casing having a U-shaped cross-section, wherein the casing is adapted to receive and retain an off-the-shelf tampon/applicator assembly therein. A handle is configured to slide along a linear rail defined by the top wall of the casing in a direction parallel to the tampon's line of action (i.e., the axis along which the tampon is expelled from the barrel of the applicator). In one embodiment, the handle is coupled to an actuator located inside the casing, flush with the proximal and of the tampon plunger. The user grasps or otherwise engages with the handle, secures the barrel of the tampon applicator in the casing (e.g., via an elastic clip or other clamp) at an analogous location to where a user would conventionally pinch the applicator barrel, navigates the distal end of the barrel to the vaginal opening and inserts the barrel into the vaginal canal up to the front (i.e., distal) end of the apparatus (i.e., such that the distal end of the casing does not enter the vaginal opening), and thereafter slides the handle in the direction of her body, resulting in the dispensing of the tampon into the vaginal canal.

Other embodiments of the present disclosure are adapted for use in inserting a tampon that is not supplied with its own applicator (also known as "digital tampons"). In these embodiments, the insertion device includes a barrel (e.g., a reusable barrel) and a plunger actuated by the slidable handle of the device. In some instances, the barrel is fastened to the distal end of the device, while in other instances the barrel is removably attached to the device in a manner similar to the embodiment described above (e.g., using a clamp provided on the casing).

Figure 2:
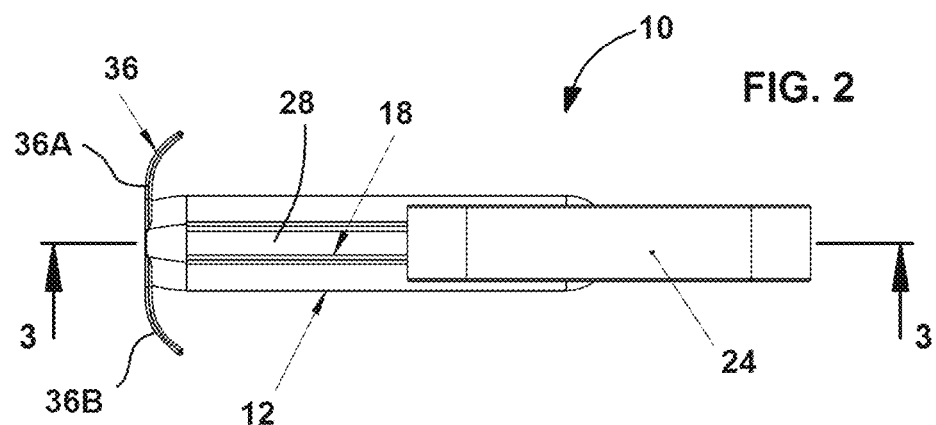
FIG. 2 depicts a top view of the embodiment of FIG. 1.

FIGS. 1 and 2 depict orthogonal and top views, respectively, of one embodiment of a tampon insertion device (10) ready for insertion of a tampon/applicator assembly therein. The tampon insertion device includes a hollow casing (also referred to as an applicator enclosure) (12) having an open distal (or front) end (14), a proximal (or back) end (16), a top wall that defines a linear rail (18), an open bottom (20) in opposition to the top wall (18), and a clamp portion (22) located at the distal end of the casing (12). The casing thus defines a chamber (13) therein (see FIG. 3). A handle (24) is slidably positioned external to the casing, and slides along the linear rail (18) of the casing (12) to expel a tampon from an applicator retained within clamp portion (22). The linear rail (18) extends parallel to the axis of actuation of the apparatus, which coincides with the axis of the tampon applicator plunger. In FIG. 1, the handle (24) is positioned at its most proximal position (at the back of the linear rail (18) of the casing (12)).

The clamp portion (22) is configured such that a conventional tampon applicator barrel can be snapped or clipped into the clamp portion (22). In the embodiment shown, the clamp portion (22) is U-shaped, and is located so that the grip portion (50) of an applicator barrel (44) can be clipped into the clamp (22). This allows the grip portion (50) to be used as a guide for clipping the tampon applicator (44) into the device at the proper location for aligning the proximal end (47) of the applicator plunger (46) with the distal face (27) of the actuator located within the casing chamber (13) (as further explained below). The compressible nature of the tampon applicator barrel (44) facilitates clamping of the clamp portion (22) onto the barrel.

Figure 3:
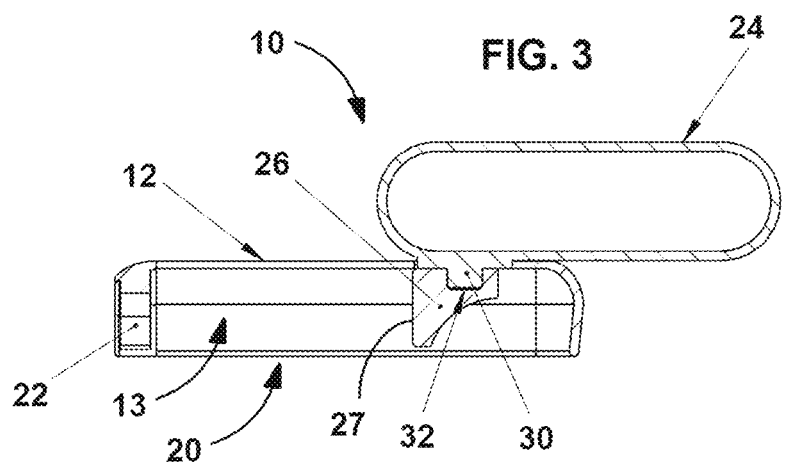
FIG. 3 depicts a cross-sectional view of the embodiment of FIG. 1, taken along the axis of actuation, which corresponds to the longitudinal centerline of the casing (identified at 3-3 in FIG. 1).
Figure 3A:
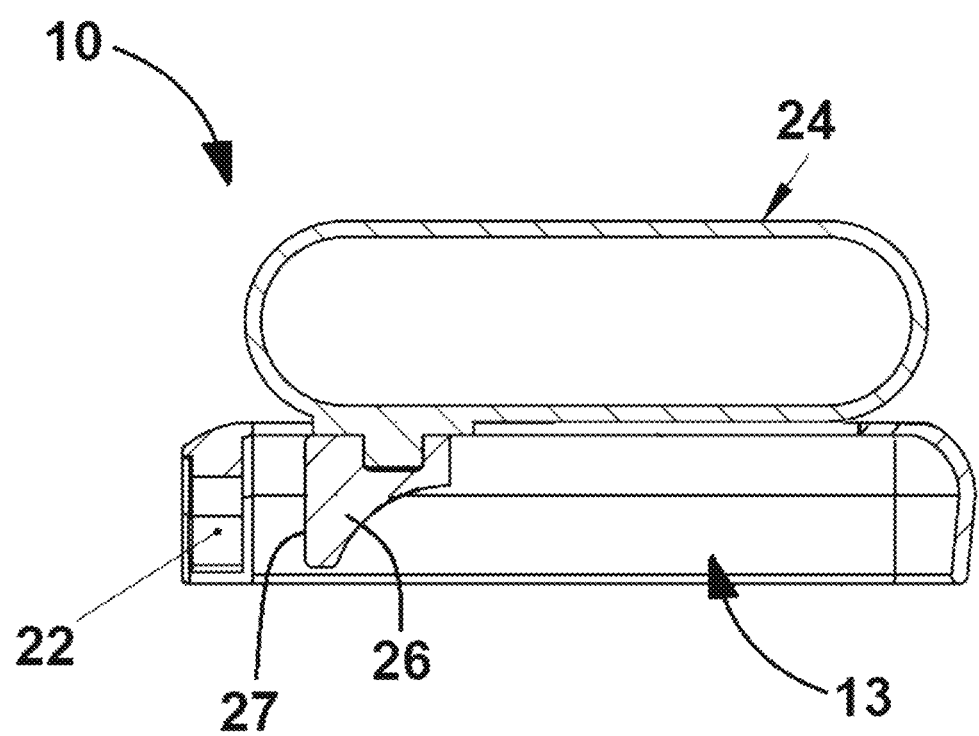
FIG. 3A is the same view as FIG. 3, but with the handle and actuator advanced distally for expelling a tampon from an applicator barrel.
Figure 4:
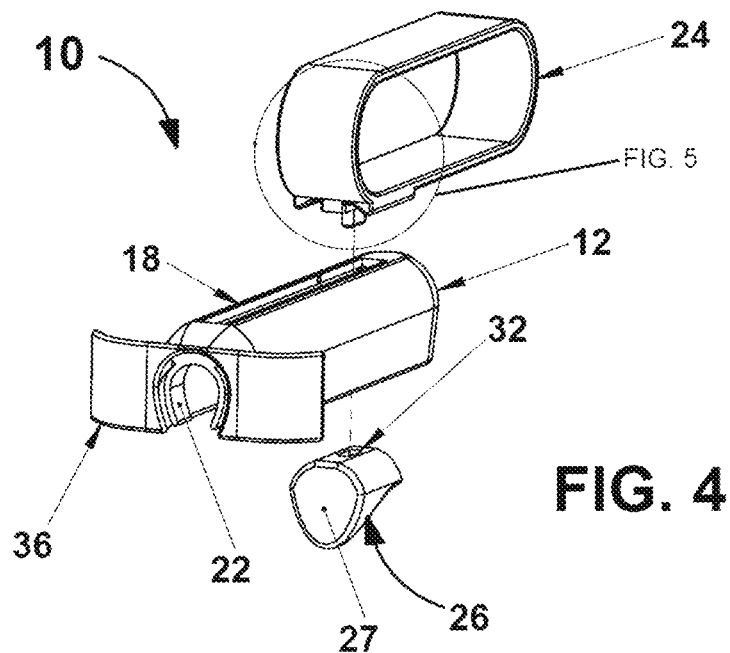
FIG. 4 depicts an exploded view of the embodiment of FIG. 1.

As best seen in the cross-sectional and exploded views of FIGS. 3 and 4, the tampon insertion device (10) further includes a plunger actuator (26) located inside the chamber (13) of the casing (12), with the actuator (26) mounted for linear movement therein (i.e., movement along the line of action of a tampon/applicator assembly clipped into the clamp portion (22)). The handle (24) is connected to the plunger actuator (26) such that linear movement of the handle with respect to the casing (12) causes a corresponding linear movement of the actuator (26) within the chamber (13). In the particular embodiment depicted, the top wall (18) of the casing (12) includes a void (28) (i.e., a slot) extending along a portion of the top wall (18), with the handle (24) connected to the actuator (26) through this void (28). It should be noted that the cross-section of FIG. 3 is taken along the centerline of the casing (12) in a plane which includes the axis (or line) of actuation of the apparatus—i.e., the actuation plane along which the handle (24) and actuator (26) are advanced in order to expel a tampon from an applicator barrel secured within the clamp (22) of the casing (12). This actuation plane also includes the axis of the tampon applicator plunger, ensuring that the plunger is actuated linearly so as to smoothly expel a tampon from the applicator barrel.

The handle (24) can be connected to the plunger actuator (26) in a variety of ways. In the exemplary embodiment shown, the handle (24) is fastened to the plunger actuator (26) by way of an assembly dowel (30) extending downwardly from the handle (24), wherein the dowel (30) is received in a corresponding socket (32) provided in the actuator (26) (e.g., a snap fit between the dowel (30) and the socket (32)). Of course a variety of other fastening mechanisms can be employed such as a screw or a nail or other complementary geometries being ultrasonically welded or secured to one another using adhesive. The handle (24) and actuator (26) are assembled such that they reside on opposing sides of the top wall (18) of the casing. With the handle (24) and actuator (26) connected through the void (28), they form a subassembly that acts as a single part such that exerting a linear actuating force on the handle (24) drives the actuation of the tampon applicator plunger (46) via the plunger actuator (26).

Figure 5:
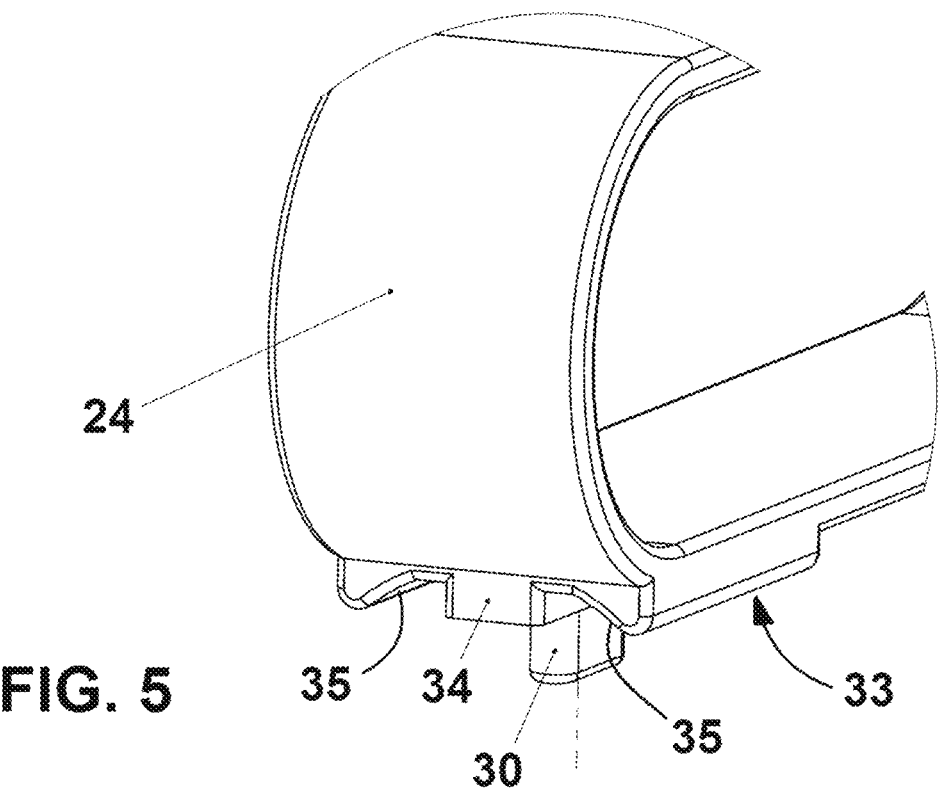
FIG. 5 depicts an enlarged view of the distal portion of the handle of the embodiment of FIG. 1.
Figure 6:
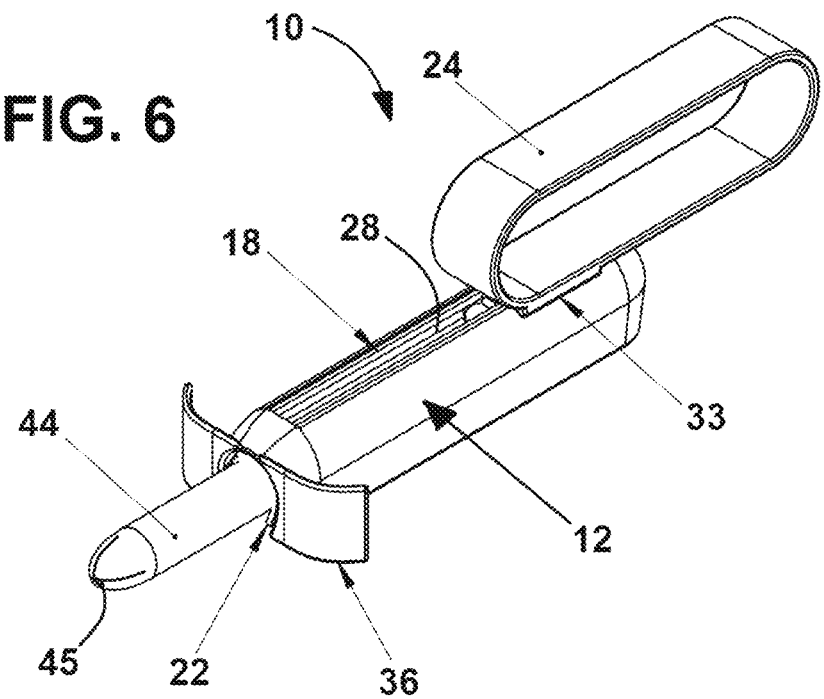
FIG. 6 depicts an orthogonal view of the embodiment of FIG. 1, with an off-the shelf tampon/applicator assembly clipped into the device and the handle at its proximal position ready to expel the tampon from the applicator.
Figure 7:
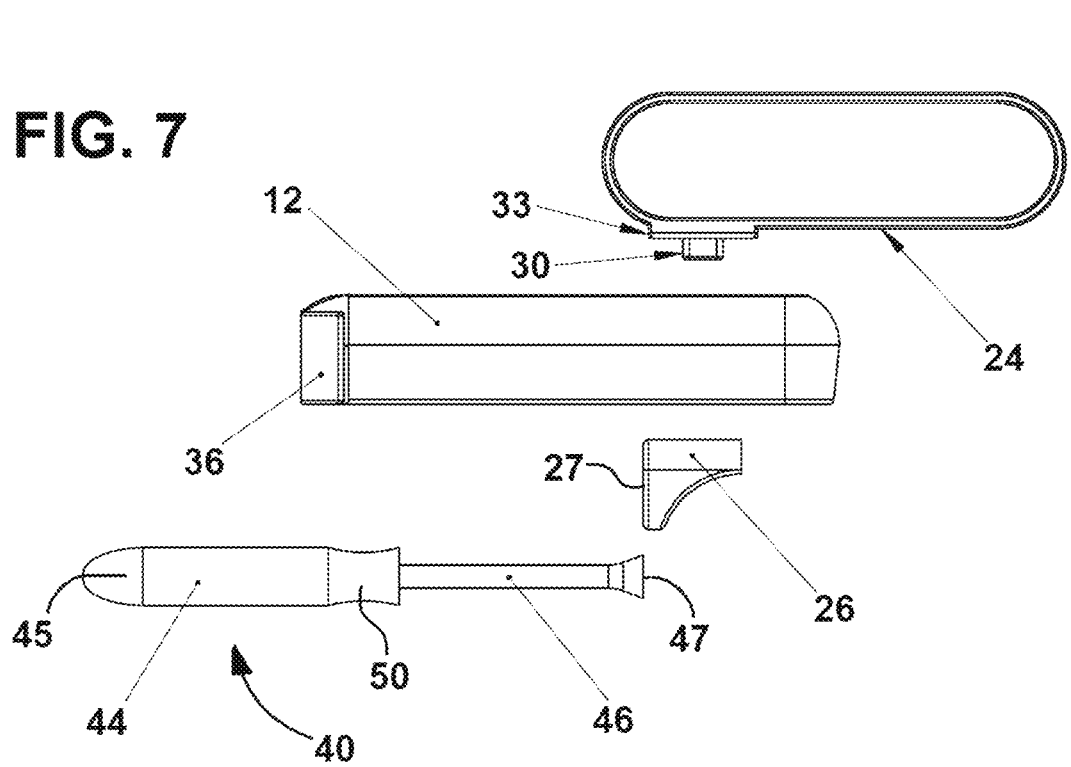
FIG. 7 depicts an exploded side view of the embodiment of FIG. 6.

As best seen in the enlarged view of the distal (or front) portion of the handle (24) shown in FIG. 5, a linear rail guide (33) is provided on the underside of the handle (24). In the exemplary embodiment, the linear rail guide (33) is located adjacent the distal underside of the handle (24), adjacent the dowel (30). It will be understood that the guide rail can be positioned at other locations on the underside of the handle (24). The underside of the linear rail guide (33) has a shape that is complimentary to the shape of the top of the casing (12), and serves to stabilize and guide the handle as it slides along the top wall (18) of the casing (12) and within the void (28). In particular, the linear rail guide (33) includes an embossment (i.e., a projection) (34) that extends into the void (28) in the linear rail (18) of the casing (12) (see FIGS. 3 and 9). The undersides (35) of the rail guide (33) along opposite sides of the projection (34) are also shaped in a manner that compliments the shape of the top wall (18) of the casing (12), such that the rail guide (33) cradles a portion of the top wall (18) of the casing with the projection (34) extending into the void (28). The linear rail guide's cohesive geometry facilitates smooth linear actuation as the user guides the handle (24) along the linear rail (18) (i.e., the top wall of the casing).

The tampon insertion apparatus depicted in FIGS. 1-6 further includes an enlarged flange portion (36) that extends laterally away from the open distal end (14) of the casing (12). In the embodiment shown, the enlarged flange portion (36) comprises first and second rounded flanges (36A, 36B) that extend laterally away from opposite sides of the casing at the open distal end (14) thereof. The flange portion (36) increases the surface area at the distal end of the tampon insertion apparatus such that the flange portion inhibits the distal (14) end of the casing (12) from entering the vaginal opening. The increased surface area provided by the flange portion (36), by not entering the vaginal opening, more efficiently facilitates an opposing normal force from the body when the handle (24) is linearly urged towards the vagina during use. These opposite forces result in a dynamic system that allows the handle (24) and plunger actuator (26) to be slid along opposite sides of the linear rail (18) towards the body while the flanged distal end of the casing remains relatively stationary.

Figure 8:
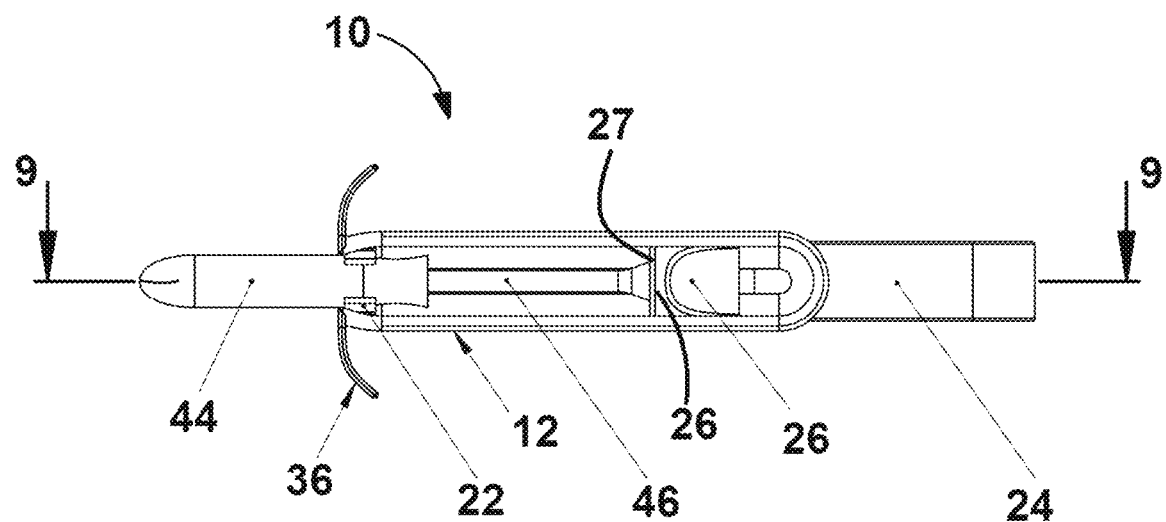
FIG. 8 depicts a bottom view of the embodiment of FIG. 6.
Figure 9:
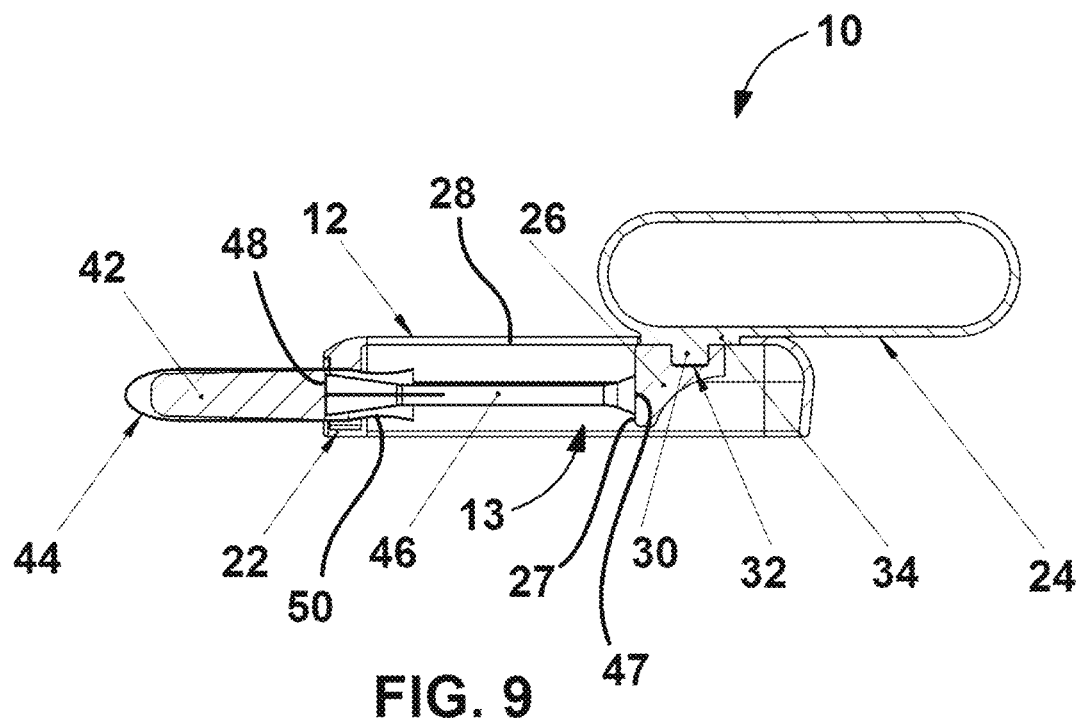
FIG. 9 depicts a cross-sectional view of the embodiment of FIG. 8, taken along the axis of actuation (identified at 9-9 in FIG. 8).

With the device in the position shown in FIGS. 1-3, the user can clip the applicator barrel (44) of a tampon/applicator assembly (40) into the clamp portion (22) by simply urging the grip portion (50) of the applicator barrel into the chamber (13) of the casing. The clamp (22) and actuator (26) are configured such that, when the handle (24) is at its proximal, retracted position and the applicator barrel is properly inserted into the clamp (12), the proximal end (47) of the plunger (46) will be positioned flush with the distal face (27) of the actuator (26), as seen in FIGS. 8 and 9. While the applicator barrel (44) can be clipped into the clamp portion (22) using two hands, the apparatus of the present disclosure is also advantageous in that this can be accomplished using only one hand, without requiring finger strength or dexterity. In particular, a tampon/applicator assembly (40) can be placed on an external surface and then, using the handle (24), the apparatus (10) is pressed over the applicator barrel (44) and plunger (46) such that the external surface on which the tampon/applicator assembly (40) rests provides the normal force necessary to snap the barrel (44) into the clamp (22). The tampon is clamped at a location that is identified in two ways. First, the clamped location is analogous to the grip location prescribed by the instructions for use of the tampon/applicator assembly. Second, the clamping location is the result of aligning the proximal end (47) of the plunger flush with the distal face (27) of the actuator (26).

Figure 10:
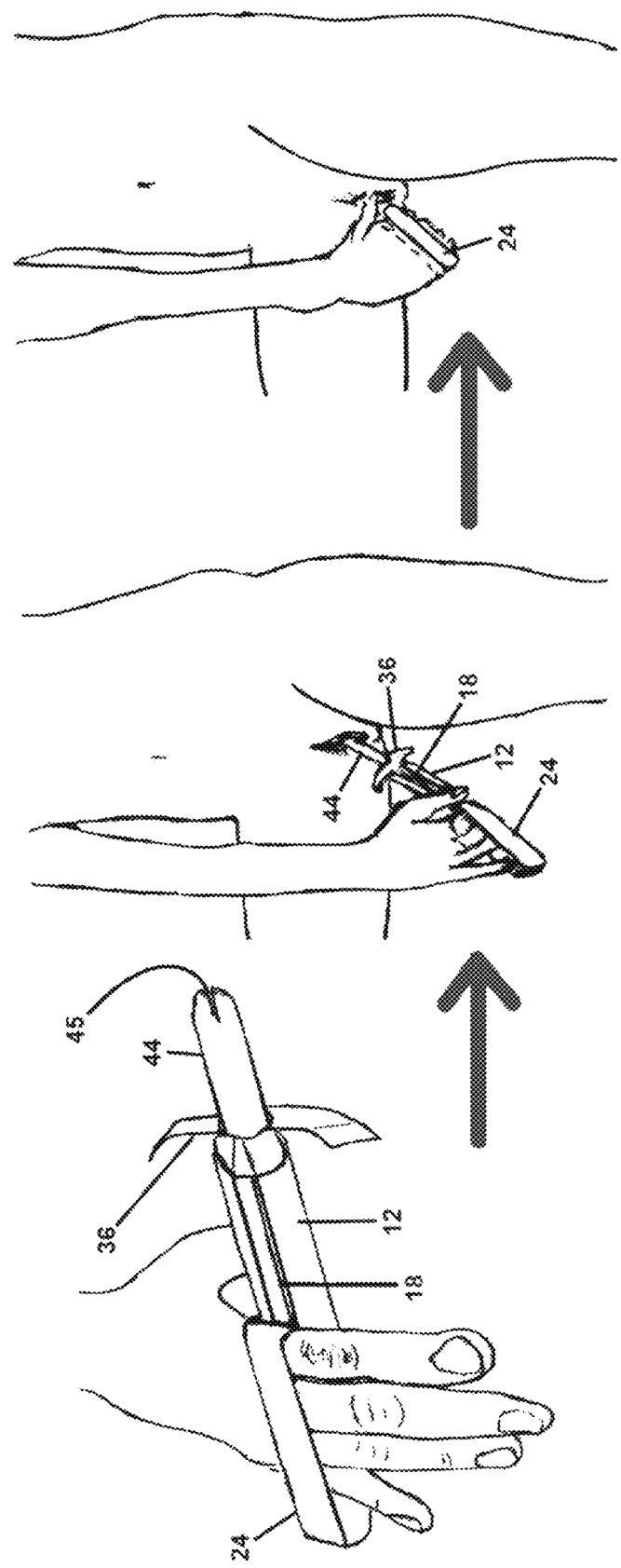
FIG. 10 depicts the sequence of using the embodiment of FIG. 6 to insert a tampon into the body.

FIG. 10 depicts sequential views of the process of a user inserting a tampon (42) into her vaginal canal using the tampon insertion device (10). With the tampon/applicator assembly (40) loaded in the device (10) (i.e., in the manner shown in FIG. 6), the user passes her hand through the loop-shaped handle (24) to allow the device (10) to be easily manipulated. The user then navigates the device (10) and attached tampon/applicator assembly (40) towards her vagina. She then inserts the exposed portion of the applicator barrel (44) into her vaginal canal, deep enough so that the contact flange (36) presses against tissue adjacent (and exterior to) the vaginal opening. Next, the user simply slides the handle (24) towards her body, such as by using arm motion only—movement of the fingers is not necessary. This results in the handle (24) sliding distally along the linear rail (18) of the casing (12), since the flange portion (36) prevents distal movement of the casing with respect to the vaginal canal. The contact flanges (36A, 36B) provide stability and increase surface area available to translate the normal force provided by the body in the direction antiparallel to the direction of action of the handle (24) and actuator (26). These opposing forces are static on the casing (12), but dynamic as the handle (24) has freedom to slide along the linear rail (18).

Because the handle (24) is fastened to the plunger actuator (26), which is resting flush against the back of the applicator plunger (46), the distal sliding of the handle (24) along the linear rail (18) urges the applicator against the proximal end (47) of the applicator plunger (46) distally so as to push the tampon (42) out of the applicator barrel (44) through opening (45) at the distal end of the barrel and into the vaginal canal. At this point, the cotton tampon [28] is secured in the body and no longer attached to its applicator or the tampon insertion aid. The device (10) can then be pulled away from the vagina and the tampon applicator barrel (44) unclipped from the device and the applicator (44) and plunger (46) disposed of.

It should be noted that the distal movement of the handle is limited by the length of the linear rail (18), particularly the void (28) therein. This prevents that actuator (26) from pushing the applicator barrel (44) out of the clamp (22). In addition, a lip or flange can be provided on the proximal end of the barrel to provide a counter force on the clamp. This feature is further described in connection with the embodiment of FIGS. 26-30.

Figure 11:
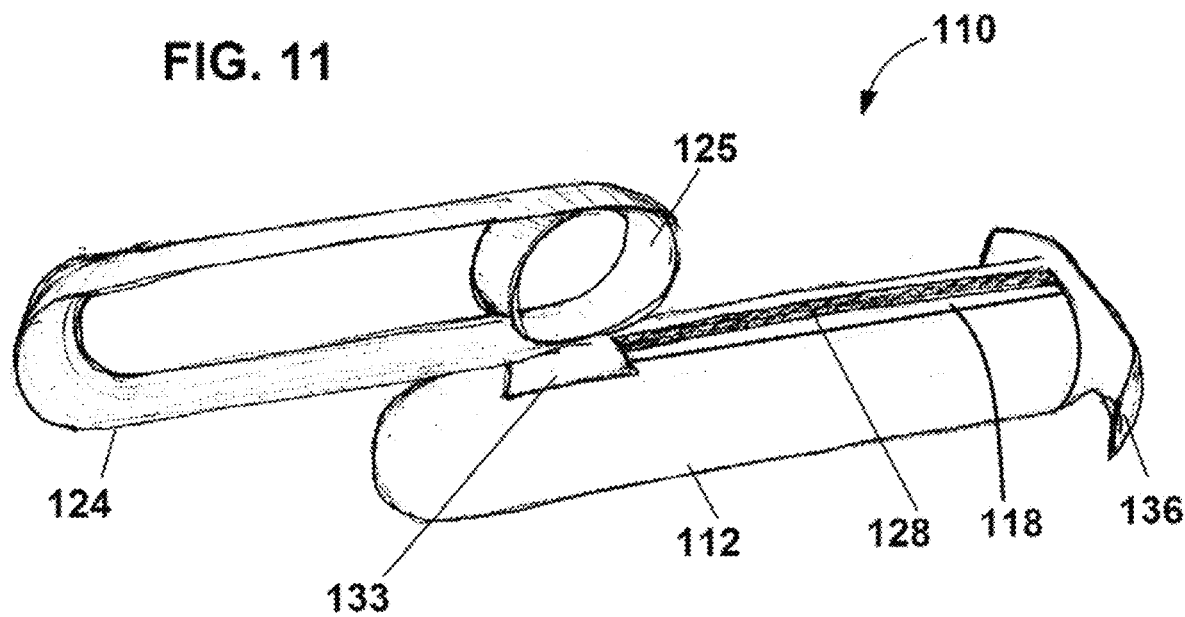
FIG. 11 depicts an alternate embodiment of a tampon insertion device according to the present disclosure.

While the handle (24) of FIGS. 1-9 is depicted as a linearly advancing, loop-shaped handle, the handle can be configured in a variety of alternative ways intended to improve the ergonomics of device manipulation and/or actuation. For example, FIG. 11 depicts an alternative embodiment of a tampon insertion device (110) wherein the loop-shaped handle (124) has been modified from that shown in FIGS. 1-9 so as to include a single-finger loop (125) at the distal end of the handle (124). This additional finger loop (125) can provide a more stable engagement of the handle (124) by the user's hand, thereby facilitating distal advancement of the handle (124) with respect to the casing. Of course one or more such finger loops can be provided, and can be positioned at one or more locations along the handle.

Figure 12:
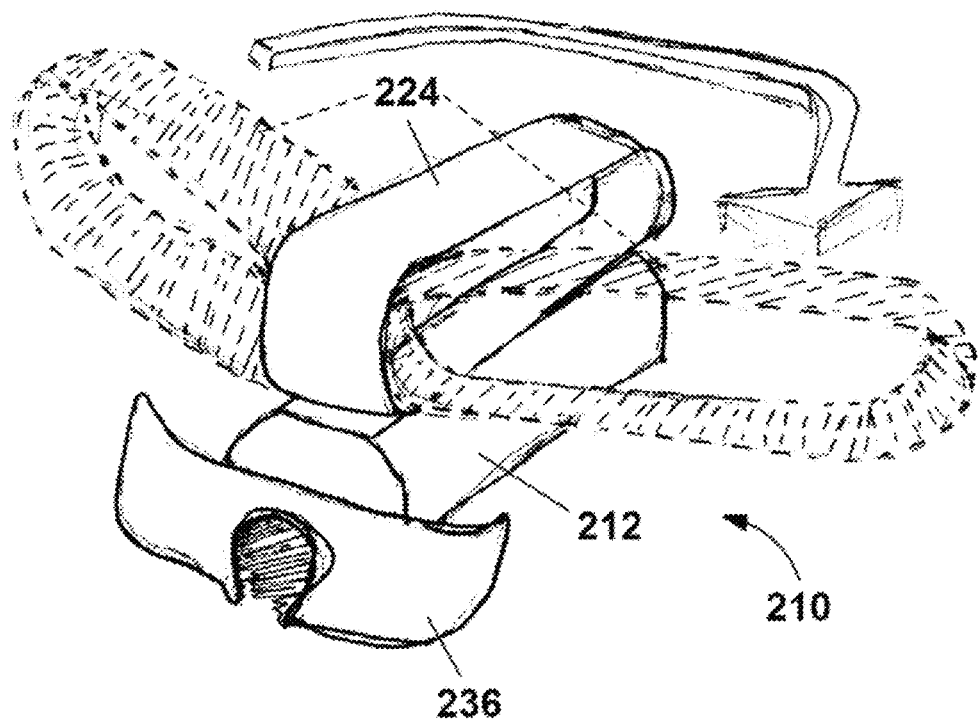
FIG. 12 depicts yet another alternate embodiment of a tampon insertion device according to the present disclosure.
Figure 13:
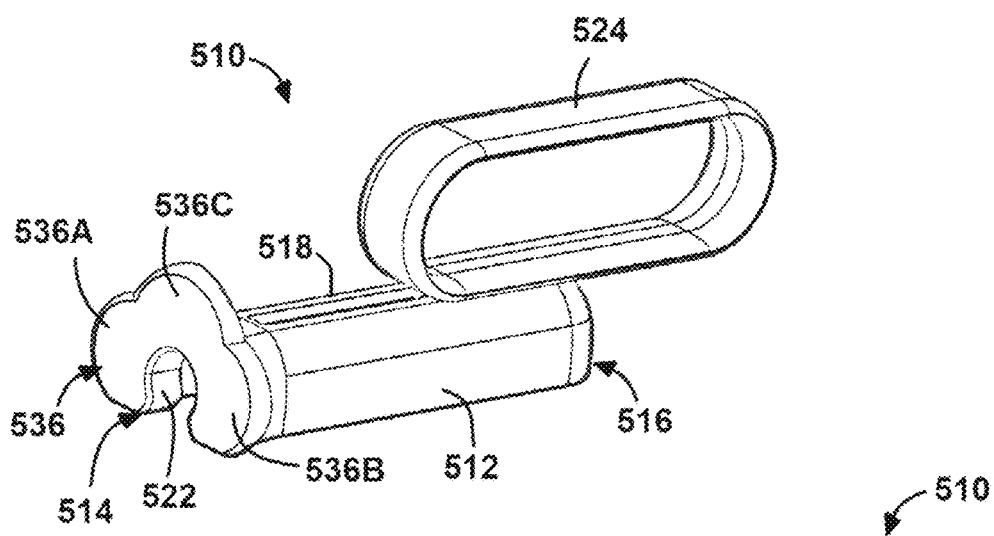
FIG. 13 depicts a front orthogonal view of another embodiment of a tampon insertion device, in the ready position primed for receiving a tampon/applicator assembly therein.

In the alternative embodiment shown in FIG. 12, the handle (224) is rotatable such that the handle (224) can be at least partially rotated to an orientation such that the length of the handle (224) is not parallel to the line of action of the device (however, the handle (224) is still linearly advanceable with respect to the casing along the actuation plane and the line of action). The rotating of the handle can be provided, for example, by a rotatable connection between the handle (224) and the internal plunger actuator (e.g., such that the handle pivots about the axis of the connection between the handle and the actuator). This rotation allows the user to manipulate the handle from a variety of angles. In the alternative embodiments of FIGS. 13-30 described below, the handle (324, 424, 524, 724) similarly can be rotatably connected to the actuator (326, 426, 526, 726) and/or modified for ergonomics (e.g., by the addition of one or more finger loops).

FIGS. 13-22 depict another alternative embodiment of a tampon insertion device (510) of the present disclosure, wherein the device (510) can be used in the same manner described above. The insertion device (510) is similar to insertion device (10) of FIGS. 1-9, with the principle differences being the configuration of the flange portion (536), the configuration of the clamp (522), the addition of a retention mechanism for releasably retaining the handle (524) in its proximal (ready) position (see FIG. 13), and a string capture slot (560) on the casing (512). Thus, tampon insertion device (510) includes a hollow casing (512) having an open distal end (514), a proximal end (516), a top wall that defines a linear rail (518), an open bottom (520) in opposition to the top wall (518), and a clamp portion (522) located at the distal end of the casing (512). A handle (524) is slidably positioned external to the casing, and slides along the linear rail (518) of the casing (512) to expel a tampon from an applicator retained within clamp portion (522). In FIG. 16A, the handle (524) is positioned at its most proximal position, such that the device (510) is ready to be loaded with a tampon/applicator assembly. In FIG. 16B, the handle (524) is positioned at its most distal position, for expelling a tampon from its applicator barrel.

Figure 16A:
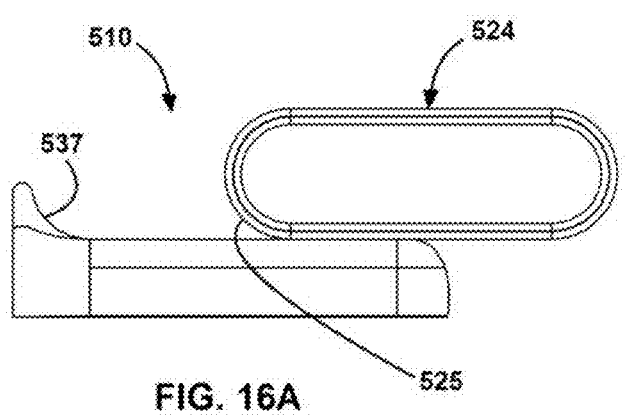
FIGS. 16A and 16B depict side views of the embodiment of FIG. 13, with FIG. 16A showing the handle in its proximal (ready) position and FIG. 16B showing the handle in its distal (deployed) position.
Figure 16B:
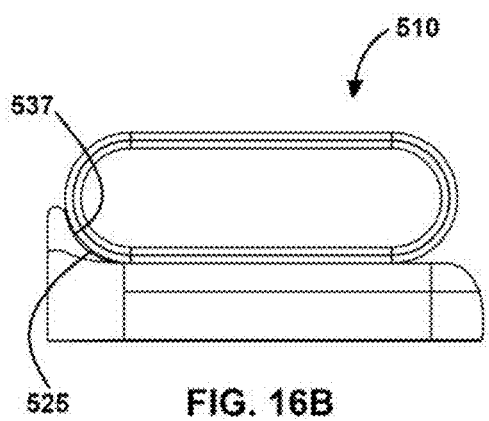
Figure 17:
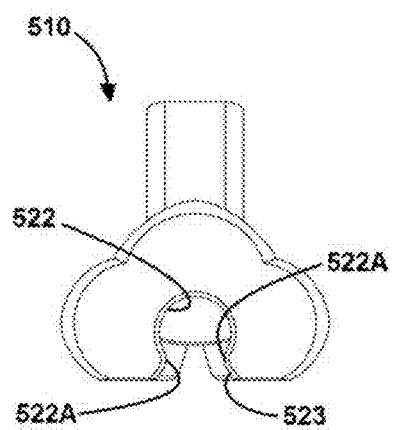
FIG. 17 depicts a front end view of the embodiment of FIG. 13.

In the embodiment of FIGS. 13-22, the clamp portion (522) is formed in the distal end (514) of the casing (512). Similar to clamp (22), clamp (522) comprises a generally U-shaped passageway, having a diameter smaller than the width of the internal chamber (513) and sized and configured to provide an interference fit with a barrel (44) of a tampon applicator. As best seen in FIG. 17, the clamp portion (522) is open at its bottom end so as to provide a clamp entrance (523), similar to claim 22) of the previously described embodiment. In this instance, however, the clamp entrance (523) is chamfered such that the width of the clamp entrance (523) increases in the downward direction (see FIG. 17). This chamfered clamp entrance (523) facilitates the securement of a tampon applicator barrel within the clamp portion (522), since this not only presents a larger entrance area but also a tapered wall that helps guide the applicator barrel into the clamp portion (522) until the barrel snaps into place past the rounded internal lips (522A) located at the upper extent of the clamp entrance (523).

The tampon insertion device of FIGS. 13-22 also includes a flange portion (536) that extends laterally away from the open distal end (514) of the casing (512). In this embodiment, the flange portion (536) has a lobed design that includes three rounded lobes (536A, 536B, 536C) that extend laterally away from the distal end (514) about the circumference of the clamp portion (522). Thus, two of the flange lobes (536A, 536B) extend laterally away from opposite sides of the open distal end (514) and the third flange lobe (536C) extends upwardly away from the open distal end, such that the flange portion (536) extends around the circumference of the clamp portion (536). The addition of the third flange lobe (536C) that extends upwardly away from the distal end portion (514) further aids in aligning the applicator barrel at the proper angle with respect to the vaginal canal. In particular, the third flange lobe (536C) helps to ensure that the barrel is not tilted downwardly with respect to the vaginal canal during use. Also, in the particular arrangement shown the distal face of the flange portion (536) is orthogonal to the line of action of the device (i.e., orthogonal to the actuation plane along which the handle (524) and actuator (526) are advanced in order to expel a tampon from an applicator barrel secured within the clamp (522)). As before, the flange portion (536) increases the surface area at the distal end (514) of the casing (512) such that the flange portion inhibits the distal end (514) of the casing from entering the vaginal opening, and also facilitates an opposing normal force from the body when the handle (524) is linearly urged towards the vagina during use.

Figure 14:
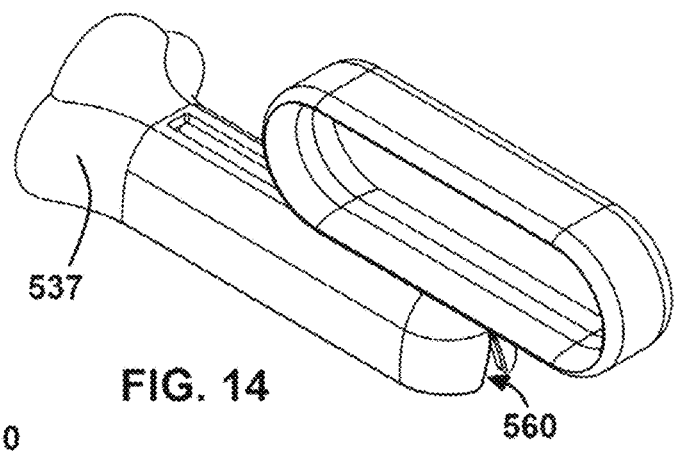
FIG. 14 depicts a rear orthogonal view of the embodiment of FIG. 13.
Figure 15:
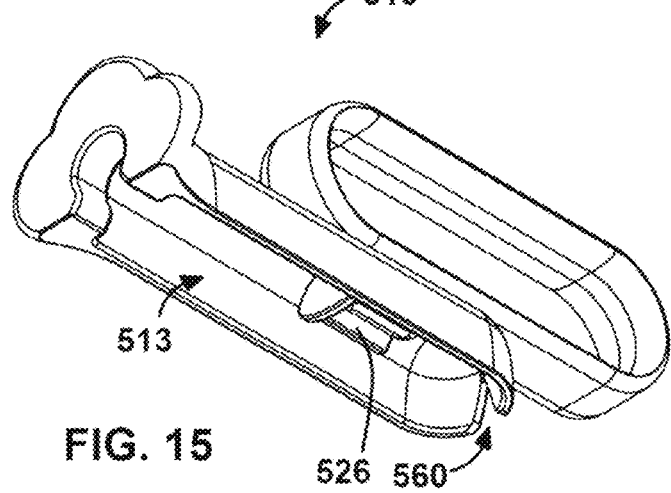
FIG. 15 depicts a bottom orthogonal view of the embodiment of FIG. 13.

The proximal face (537) of the flange portion (536) is outwardly flared (i.e., trumpeted), as best seen in FIGS. 14 and 16A. This outward flaring, particularly when combined with the tri-lobed flange arrangement, not only provides an aesthetically pleasing appearance (similar to a flower), but also allows the flange portion (536) to increase in thickness towards the casing (512) without significantly restricting the distal travel of the loop-shaped handle (524). As seen in FIG. 16B, the curvature of the proximal face (537) of the flange portion (536) generally corresponds to that of the lower distal end (525) of the handle (524), as seen in FIG. 16B, thereby increasing the distal travel of the handle. In one embodiment, contact between the lower distal end (525) of the handle (524) and the proximal face (537) of the flange portion (536) serves to limit the forward (distal) travel of the handle for preventing the plunger actuator (526) from ejecting the applicator barrel from the clamp member. In other embodiments, the length of the slot (528) in the linear rail (518) of the casing can be selected so as to limit the forward travel of the handle. As yet another alternative, a structure within the chamber (513) (e.g., an internal wall or other projection) can be arranged so as to limit forward movement of the actuator (526).

Like the previously described embodiments, tampon insertion device (510) further includes a plunger actuator (526) located inside the chamber (513) of the casing (512), with the actuator (526) mounted for linear movement therein (i.e., movement along the actuation plane and the line of action of a tampon/applicator assembly clipped into the clamp portion (522)). The handle (524) is connected to the plunger actuator (526) such that linear movement of the handle with respect to the casing (512) causes a corresponding linear movement of the actuator (526) within the chamber (513). The top wall (518) of the casing (12) includes a void (528) (i.e., a slot) extending along a portion of the top wall (518), with the handle (524) connected to the actuator (526) through this void (528). The handle (524) is connected to the plunger actuator (526) by a dowel (530) (in the form of an elongate projection) extending downwardly from the handle (524), wherein the projection (530) is received and secured in a corresponding socket (532) provided in the top surface of the actuator (526) (e.g., via a snap fit or one of the other mechanisms previously described). The handle (524) and actuator (526) are assembled such that they reside on opposing sides of the top wall (518) of the casing. When the handle (524) and actuator (526) are connected through the void (528), they form a subassembly that acts as a single part such that exerting a linear actuating force on the handle (524) drives the actuation of the tampon applicator plunger (46) via the plunger actuator (526).

Figure 21:
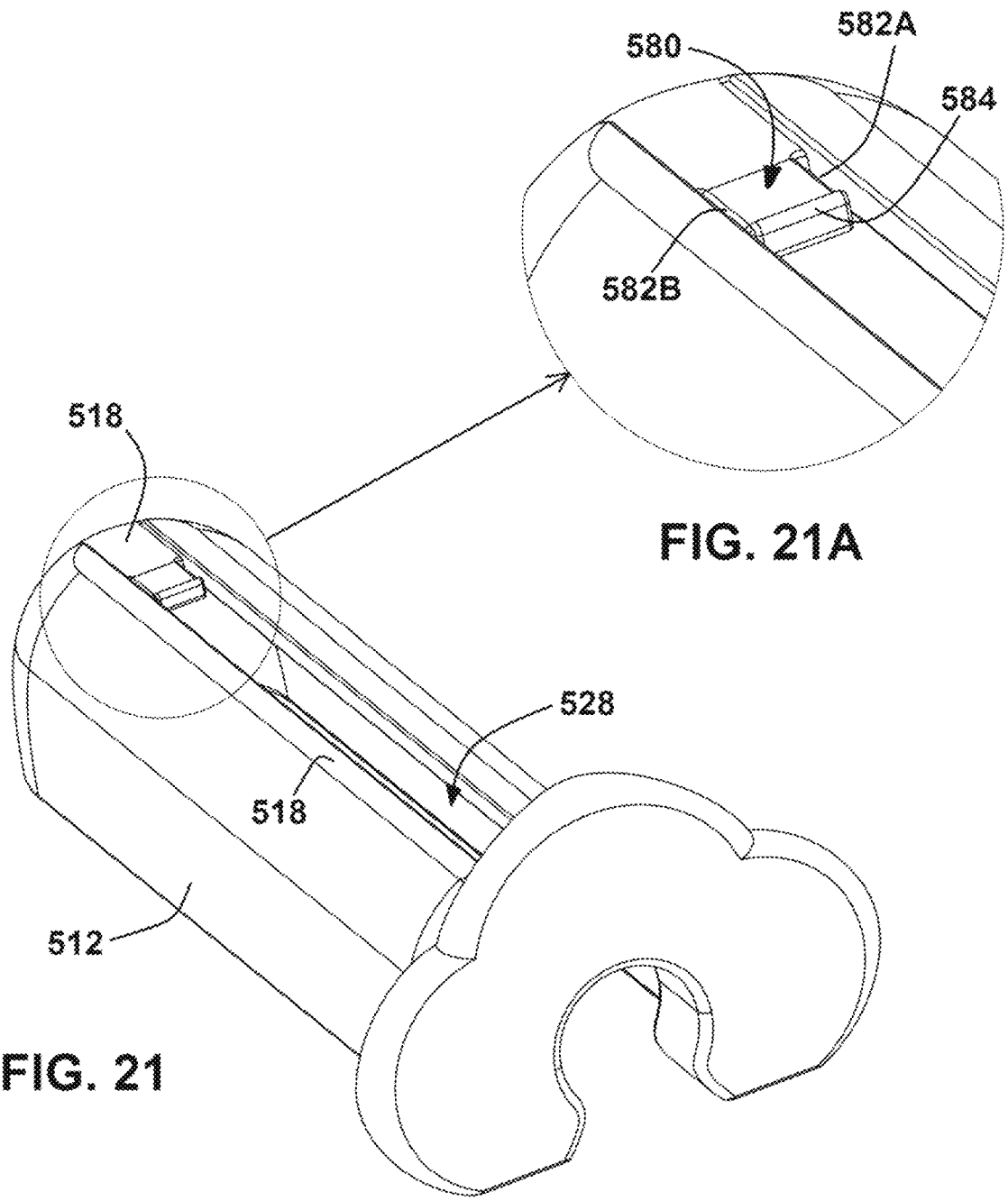
FIG. 21 depicts an orthogonal view of the casing of the embodiment of FIG. 13.
Figure 22:
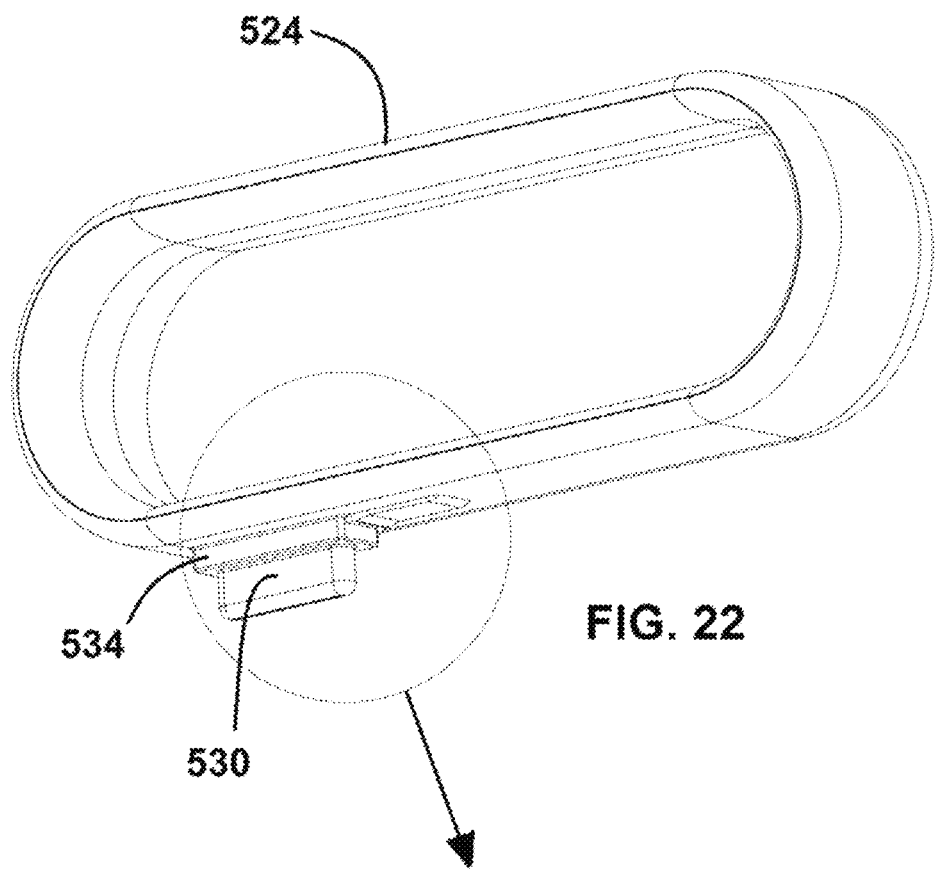
FIG. 22 depicts an orthogonal bottom view of the handle of the embodiment of FIG. 13.
Figure 22A:
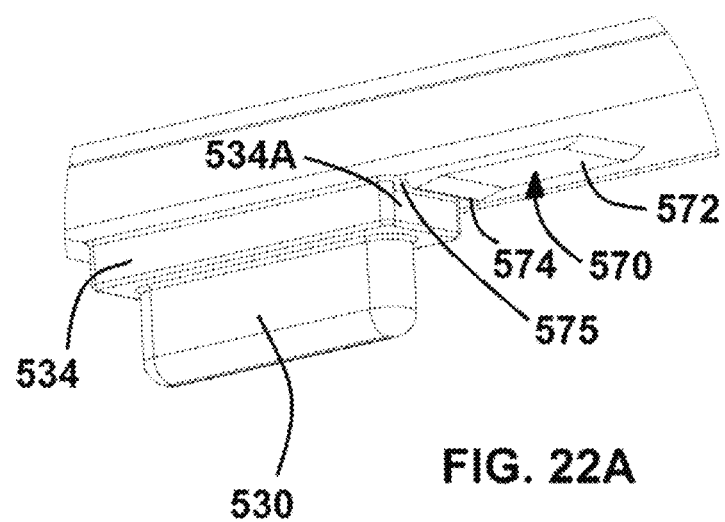
FIG. 22A depicts an enlarged view of the indicated portion of FIG. 22.

As best seen in the enlarged view of the distal (or front) portion of the handle (524) shown in FIG. 22A, the embodiment of FIGS. 13-22 also includes a linear rail guide in the form of a projection (534) that extends downwardly away from the distal bottom surface of the handle (524). As before, the projection (534) is configured to extend into the void (528) in the linear rail (518) of the casing (512) in order to guide movement of the handle with respect to the linear rail (518). If desired, the rail guide on the handle (524) can be further configured similar to the rail guide of the previous embodiment (i.e., so as to include additional side projections that extend over portions of the top wall of the casing, as seen in FIG. 5).

The embodiment of FIGS. 13-22 further includes a slide retention mechanism that retains the handle (524) (and hence the actuator (526)) in its proximal, retracted position to facilitate tampon loading, while still allowing the handle to be advanced distally by the user. As best seen in the enlarged view of FIG. 22A, a retention member (570) is provided on the bottom surface of the handle (524) proximal to the guide projection (534). The retention member (570) includes a first flat section (572) that extends downwardly away from the bottom surface of the handle (524), and a deflection rib (574) immediately distal to the first section (572), wherein the deflection rib (574) extends downwardly away from the bottom surface of the handle (524) a greater extent than the first flat section (572) (i.e., the deflection rib (574) is greater in height than the first flat section (572)). The deflection rib (574) is also spaced away from the proximal end (534A) of the guide projection (534) such that a gap (575) is provided therebetween.

The retention member (570) is configured to releasable engage with an engagement member. In this example, the engagement member comprises a deflectable, cantilevered beam (580) located at the proximal end of the void (i.e., slot) (528) in the top wall (518) of the casing (see FIGS. 21 and 21A). As best seen in the enlarged view of FIG. 21A, the proximal end of the cantilevered beam (580) is fixed to the top wall (518) of the casing (512), adjacent the proximal end of the casing. The sidewalls (582A, 582B) of the cantilevered beam (580) are spaced away from the interior sidewalls of the void (528) such that the beam (580) is deflectable downwardly into the slot (528). A locking rib (584) is provided at the distal end of the cantilevered beam (580). As the handle (524) is slid proximally (i.e., from the position in FIG. 16B towards the position in FIG. 16A), the first flat section (572) of the retention member (570) on the handle will pass over the locking rib, causing the cantilevered beam (580) to deflect downwardly into the slot (528), thereby preloading the deflectable (i.e., flexible) beam (580). As the handle (524) is further slid proximally, the deflection rib (574) will advance over the locking rib (584) of the beam (580), causing the beam to deflect further downwardly. As the handle is slid even further in the proximal direction, the deflection rib (574) on the handle will move past the locking rib (584), allowing the cantilevered beam (580) to return towards its undeflected position (FIG. 21). As a result, the locking rib (584) will enter the gap (575) between the deflection rib (574) and the proximal end (534A) of the guide projection (534) on the underside of the handle (524). As a result, the locking rib (584) will impede distal movement of the handle (524) until sufficient force is applied to the handle during use to allow the deflection rib (574) to pass over the locking rib (584) by deflecting the beam (580) downwardly into the slot (528). As also seen in FIGS. 21A and 22A, the walls of the deflection and locking ribs (574, 584) are angled in order to facilitate movement past one another.

It will be understood that a variety of alternative forms of slide retention mechanisms can be used in place of the retention member and cantilevered beam arrangement. By way of example, one or more magnetic regions can be provided on the casing and/or on the handle, along with complementary magnetic (i.e., opposite polarity) or ferrous regions on the other of the handle and/or casing. These magnetic/ferrous regions are located so as to retain the handle in its proximal position, while still allowing the handle to move distally when sufficient force is applied thereto.

The embodiment of FIGS. 13-22 further includes a string capture slot (560) on the casing (512), which may be used to assist in removing a tampon. In particular, tampon strings typically have a knot tied into the free end of the string. While the string is used to remove a tampon from the vaginal canal, this may be difficult for some women—particularly if they have limited finger strength or dexterity. The string capture slot (560) on the insertion device (510) can be used to capture the knot of the tampon string therein, thus allowing the device (510) to be used to pull the tampon out of the vaginal canal.

Figure 18:
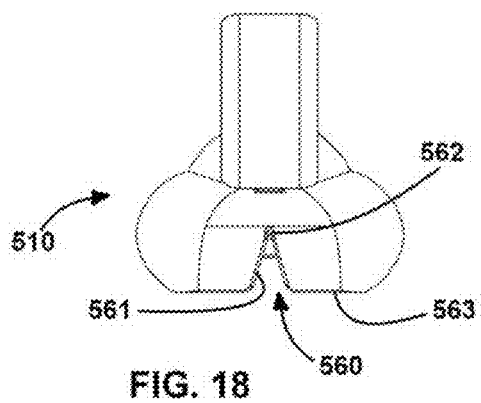
FIG. 18 depicts a rear end view of the embodiment of FIG. 13.
Figure 19:
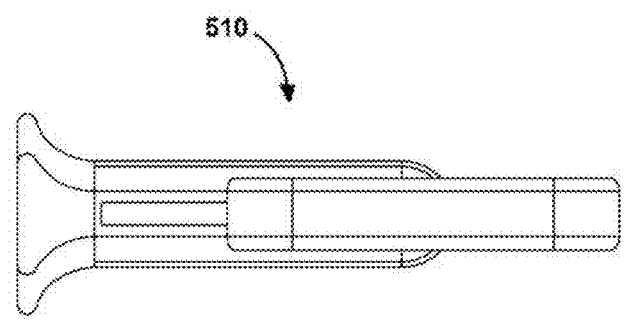
FIG. 19 depicts a top view of the embodiment of FIG. 13.
Figure 20:
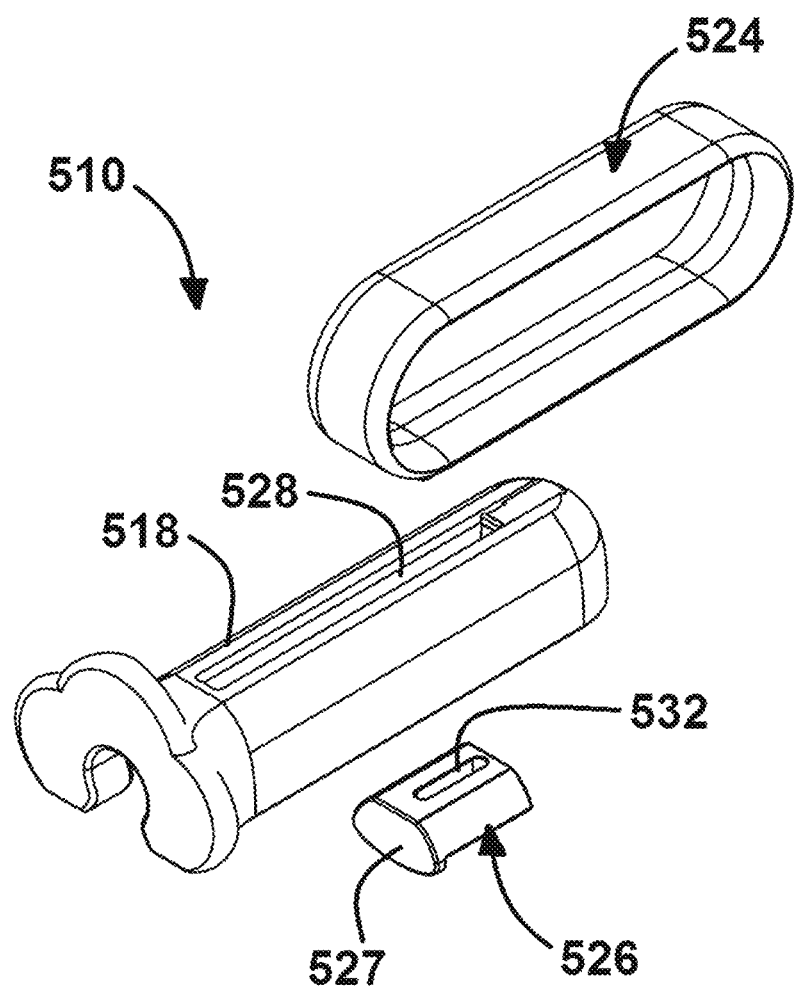
FIG. 20 depicts an exploded view of the embodiment of FIG. 13.

As best seen in FIG. 18, the string capture slot (560) is located in the proximal end wall of the casing (512) (although it could be located elsewhere on the device). The string capture slot (560) includes a first portion (561) that extends upwardly from the bottom edge (563) of the proximal end of the casing (512), which terminates in a second portion (562). The first portion (561) of the capture slot tapers in width towards the second portion (562) of the slot, while the second portion (562) has a generally constant width that is less than that of a typical tampon string knot but slightly larger than the typical width of the untied string (e.g., about 2 to about 2.5 mm in width). To use the device (510) for tampon removal, the device is placed over the tampon string such that the string moves into the capture slot (560) and bottoms out in the second portion (562) of the slot. The device is then slid down the removal string until the knot I the string reaches the slot (560). The user can then simply pull the device away from the vaginal opening, causing the tampon removal string to be pulled away from the user's vagina—thus removing the tampon.

Figure 23:
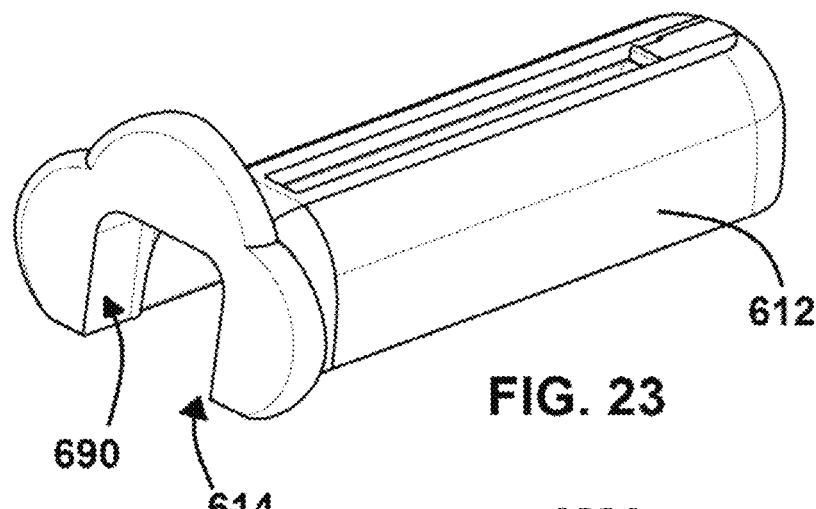
FIG. 23 depicts an orthogonal view of an alternative embodiment of the casing for use in the embodiment of FIG. 13.
Figure 25:
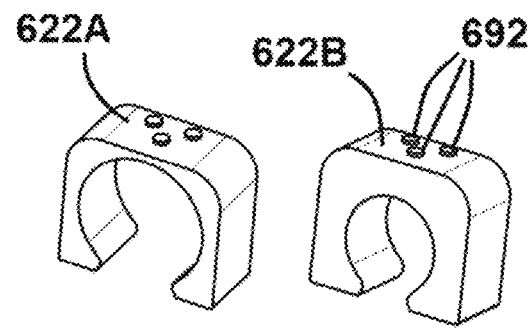
FIG. 25 depicts a pair of magnetically mountable clamp inserts for use with the casing of FIG. 23.
Figure 24:
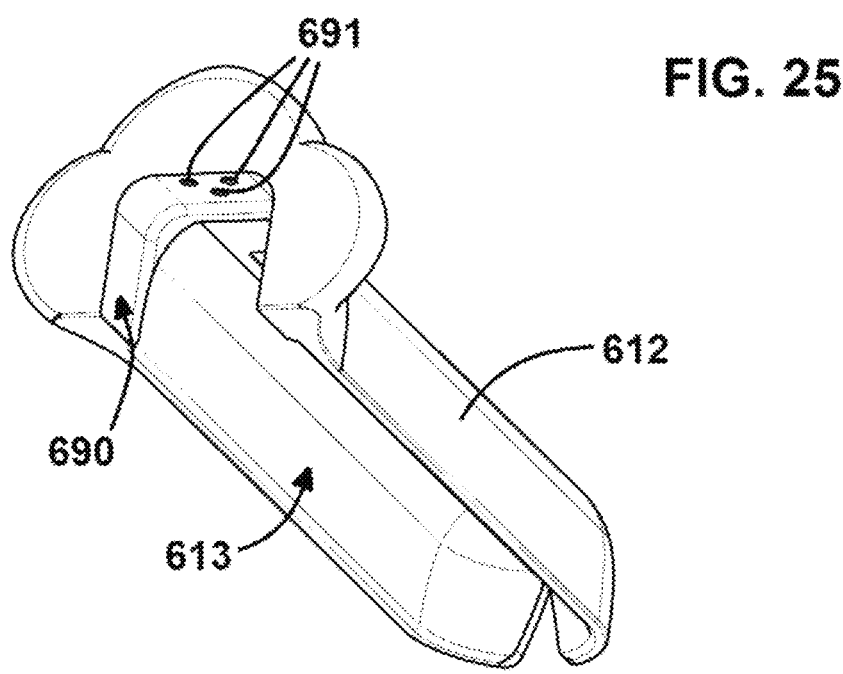
FIG. 24 depicts a bottom orthogonal view of the casing of FIG. 23.

While the tampon insertion device (10, 110, 210, 510) can be manufactured in two or more configurations to accommodate size differences in the applicator barrels of tampon/applicator assemblies from different manufacturers, FIGS. 23 and 24 depict an alternative configuration of a casing (612) that may be used in place of casing (512) in the embodiment of FIGS. 13-22 (or in place of casing (712) in FIGS. 27-30). In this instance, the casing (612) is configured such that the clamp for securement of an applicator barrel within the casing is provided a selected one of two or more clamp inserts (622A, 622B) of differing sizes that are removably mountable within a clamp recess (690) formed in the distal end (614) of the casing (612). Each of the clamp inserts (622A, 622B) is configured similar to clamp (522), comprising a generally U-shaped passageway having a diameter smaller than the width of the internal chamber (613) and sized and configured to provide an interference fit with a barrel (44) of a tampon applicator. As seen in FIG. 25, the internal diameter of the clamp insert (622A) is larger than that of the clamp insert (622B), and therefore is used for applicators having larger diameter barrels.

The external size and shape of the clamp inserts (622A, 622B) are identical, and match that of the clamp recess (690) in the distal end of the casing (612). In the example shown, the clamp inserts (622A, 622B) and clamp recess (690) have a rectangular configuration such that each of the clamp inserts (622A, 622B) can be selectively and matingly secured within the clamp recess (690). It will be understood that the clamp inserts (622A, 622B) and clamp recess (690) can have any of a variety of other matching configurations such as square, polygonal, oval, circular, etc.

The clamp inserts (622A, 622B) and the clamp recess (690) include retention features for releasably retaining a selected one of the clamp inserts within the recess for use of the device. In the example shown, one or more magnets (691) are provided in or on the upper interior wall of the clamp recess (690) and corresponding magnets (692) of opposite polarity to that of magnets (691) are provided in or on the upper wall of the clamp inserts (622A, 622B). In this manner, the magnetic attraction between the aligned magnets (691, 692) will retain the clamp insert (622A, 622B) in place within the clamp recess (690) with sufficient force to allow use of the device, but still be removable so that a different size clamp insert can be inserted into the clamp recess (690).

Alternatively, the retention features (e.g., magnets (691, 692) can be configured for permanent mounting of one of the clamp inserts (622A, 622B) within the clamp recess (690). In this arrangement, the tampon insertion device can be manufactured as a kit containing two or more sized of clamp inserts (622A, 622B), such that the end user can then select the appropriately sized clamp insert for permanent mounting within the clamp recess (690) based on her preferences.

It will also be understood that various other types of retention mechanisms can be used to removably or permanently mount one of two or more sizes of clamp inserts (622A, 622B) within the clamp recess (690). These retention mechanisms include, for example, hook-and-loop fasteners, or high friction surfaces on the engaging surfaces of clamp inserts and the clamp recess.

Tampons are also available without an applicator (also known as "digital tampons"). Such digital tampons typically comprise a cotton (or other absorbent material) tampon along with an attached string for removal of the tampon after use. Embodiments of the present disclosure are configured for aiding in the insertion of digital tampons, and one such embodiment is depicted in FIGS. 26-30. In this embodiment, the tampon insertion device (710) includes a casing (712) and a handle (724) that are configured similar to the casing (512) and handle (524) in FIGS. 13-22. Thus, the casing (712) includes a tri-lobed flange portion (736) that extends laterally away from the open distal end (714) of the casing (712). The hollow casing (712) once again defines an internal chamber (713) (see FIG. 30), as well as a top wall that defines a linear rail (718). The handle (724) is slidably positioned external to the casing, and slides along the linear rail (718) of the casing (712) to expel a tampon from the distal end of the device. In FIG. 27, the handle (724) is positioned at its most proximal position, such that the device (710) is ready to be loaded with a tampon. In FIGS. 29 and 30, the handle (724) is positioned at its most distal position, for expelling a tampon from the distal end of the device (710).

As in the embodiment of FIGS. 13-22, a clamp portion (722) is formed in the distal end (714) of the casing (712). Clamp (722) comprises a generally U-shaped passageway, having a diameter smaller than the width of the internal chamber (713) and is sized and configured to provide an interference fit with a reusable barrel (744) (described below). The clamp portion (722) is open at its bottom end so as to provide a clamp entrance, similar to the clamp (522) of the previously described embodiment.

In the embodiment of FIGS. 26-30, the handle (724) is connected to an actuator assembly (726) (further described below) by an elongate projection (730) that extends downwardly from the handle (724), wherein the projection (730) is received and secured in a corresponding socket (732) provided in the drive carriage (729) of the actuator assembly (726) (e.g., via a snap fit, adhesive, ultrasonic welding, or one of the other mechanisms previously described). The handle (724) and drive carriage (729) are assembled such that they reside on opposing sides of the top wall (718) of the casing. With the handle (724) and drive carriage (729) connected through the void (728), they form a subassembly that acts as a single part such that exerting a linear actuating force on the handle (724) drives the expelling of the tampon via the actuator assembly (726).

As with the embodiment of FIGS. 13-22, a linear rail guide in the form of a projection (734) that extends downwardly away from the distal bottom surface of the handle (724) is provided, and is configured to extend into the void (728) in the linear rail (718) of the casing (712) in order to guide movement of the handle with respect to the linear rail (718). Thus, as in the previous embodiments, the projection (734) freely slides within the void (i.e., slot) (728). If desired, the rail guide on the handle (724) can be further configured similar to the rail guide of the embodiment of FIGS. 1-9. The embodiment of FIGS. 26-30 further includes a slide retention mechanism for releasably retaining the handle (724) (and hence the actuator assembly (726)) in its proximal, retracted position to facilitate tampon loading, while still allowing the handle to be advanced distally by the user. The slide retention mechanism in this embodiment is configured identical to that of FIGS. 13-22, however, it will be understood that a variety of alternative mechanism can be employed.

Since digital tampons are provided without an applicator barrel, the tampon insertion device (710) includes a reusable barrel (744) that is configured similar to that of a conventional tampon applicator. It should be noted that barrel (744) can also be configured to be disposable, intended for a single use. In such instances, the barrel can be sterile packaged to ensure sterility. For a reusable barrel (744), the barrel is preferably made of a suitable, biocompatible material that can be readily cleaned by the end user while providing sufficient structural integrity for multiple used—e.g., biocompatible materials that can be cleaned and/or sanitized using, for example alcohol, antibacterial soaps or other disinfectants/sanitizers. Suitable materials for the barrel (744) include, for example, medical grade silicone, thermoplastic elastomers (e.g., Mediprene), and antimicrobial Sanipolymers.

Figure 26:
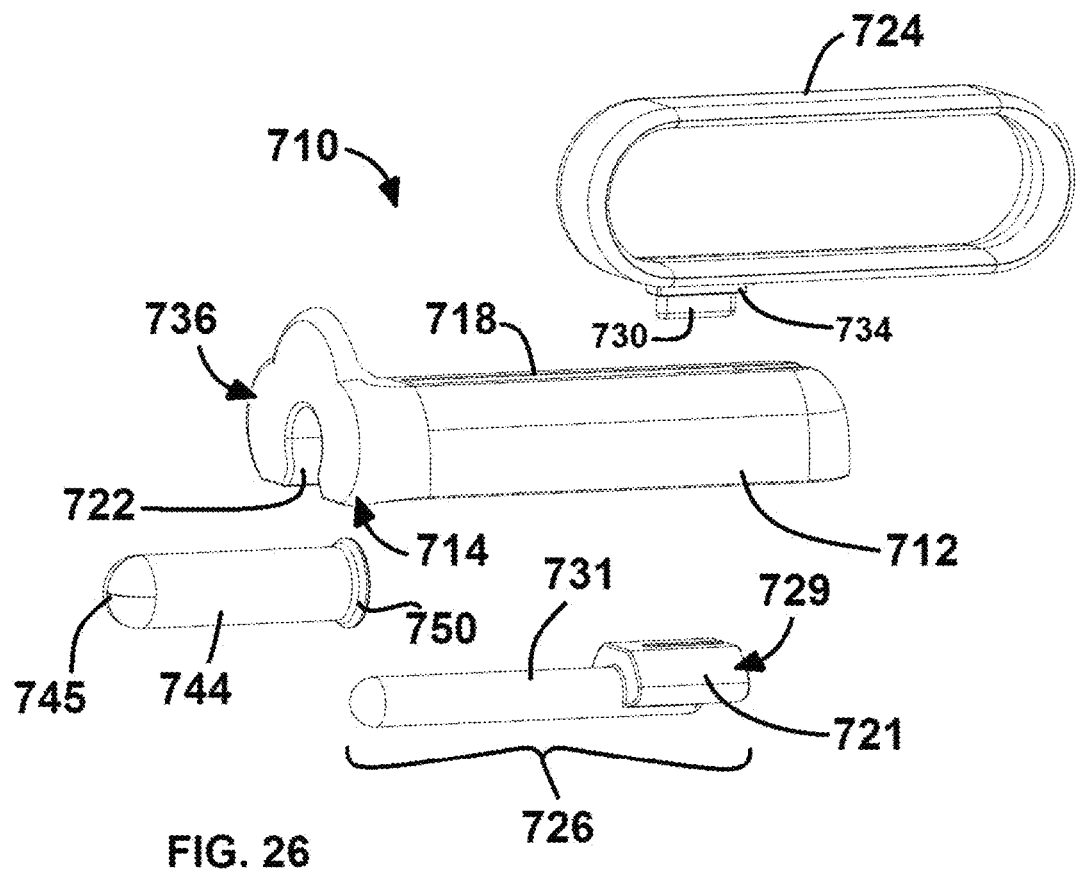
FIG. 26 depicts an exploded front view of alternative embodiment of a tampon insertion device according to the present disclosure.
Figure 27:
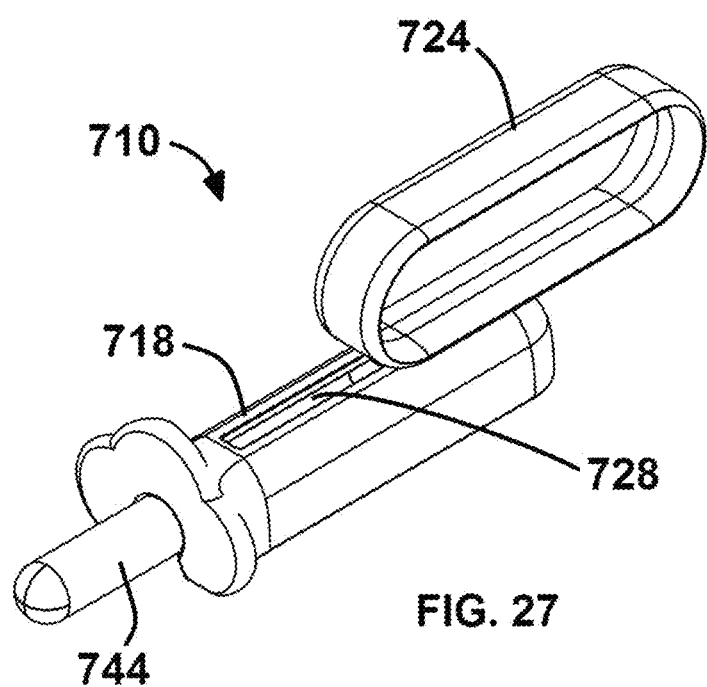
FIG. 27 depicts a top orthogonal view of the assembled embodiment of FIG. 26.

As best seen in FIGS. 26 and 28, barrel (744) is generally cylindrical, with an open proximal end (751), and a domed distal end wall (743) having an opening (745) through which a tampon can be expelled Like a conventional tampon applicator barrel, the opening (745) in the distal end wall (743) of barrel (744) can be provided by an arrangement of slits that meet at the distal tip of the barrel so as to form petals. Thus, when the distal end of a tampon is urged against the inner surface of the distal end wall (743), the opening (745) in the distal end wall (743) is forced open to allow the tampon to be expelled. In the depicted embodiment, the tampon barrel (744) is made of a biocompatible, resilient polymer that allows the opening (745) (i.e., the petals formed by the plurality of slits) to return to its closed position after a tampon has been expelled therefrom.

A flange (750) is provided at the proximal end of the barrel (744). The flange (750) not only serves as a guide for the insertion of the barrel (750) into the clamp portion (722) on the casing, it also helps to prevent the barrel (750) from being inadvertently pushed out of the clamp (722). As best seen in the bottom view of FIG. 30, the barrel is clipped into the clamp portion (722) such that the flange (750) is located immediately proximate to the clamp (722) within the chamber (713). The diameter (D) (see FIG. 30) of the barrel (744) distal to the flange (750) is slightly larger than the inner diameter for the clamp portion (722) such that the barrel is compressed slightly when clipped into the clamp portion (722) to facilitate retention of the barrel within the clamp.

The actuator assembly (726) of the embodiment of FIGS. 26-30 includes a drive carriage (729) and an elongate plunger (731) extending distally away from the drive carriage (729). The drive carriage (729) can be configured similar to the actuator (526) of the previous embodiment, with its top surface (i.e., the surface in which the socket (732) is provided) and its upper sidewalls (721) configured to match the shape of the interior walls of the chamber (713) of the casing (712) in order to facilitate a smooth, linear motion of the drive carriage (729) within the casing. The elongate plunger (731) extends distally away from the drive carriage, in alignment with the axis of actuation of the device (710). the plunger (731) may be integrally formed with the drive carriage (729), or may be separately formed and attached thereto (e.g., by adhesive or ultrasonic welding). The length and position of the plunger (731) and the travel of the drive carriage (729) and handle (724) are configured so that full distal travel of the handle (724) (FIG. 29) results in the distal end of the plunger (731) being driven substantially to the interior distal end of the barrel in order to fully expel a tampon from the distal end of the barrel.

To use the embodiment of FIGS. 26-30, a digital tampon is loaded into the barrel (744) with the tampon string extending out the open proximal end (751) of the barrel. Next, with the device (710) in the position shown in FIG. 27, the user clips the barrel (744) into the clamp portion (72) by simply urging the applicator barrel into the clamp with the flange (750) located inside the chamber (713) immediately proximal to the clamp (722). At this point the loaded device (710) can be used to insert the tampon into the vaginal canal in the manner described previously. The handle (724) is slid distally along the linear rail (718) of the casing (712), resulting in linear movement of the plunger along the central axis of the tampon (and the axis of actuation of the device) so as to expel the tampon into the vaginal canal. The barrel (744) can then be removed from the device (710) for cleaning and storage for subsequent use.

The barrel can be provided with various features to facilitate proper insertion of the barrel (744) into the clamp (722), as well as to improve the retention of the barrel within the clamp. For example, the exterior of the barrel at the intended clamping location can be textured (e.g., ribbed or other surface roughening) to improve grip within the clamp as well as by the user. The barrel can also be marked (e.g., a strip or other marking in a contrasting color) to identify the proper clamping location. As an alternative to barrel (744) being loaded into the casing (712) of the insertion device (710), it is also contemplated that the barrel can be fastened to the distal end of the device (either within the casing or fastened to the exterior of the casing).

The present invention has been described in terms of several particular embodiments and applications, both in summarized and detailed form. However, it is not intended that development of a tampon insertion aid is limited to the scope of these embodiments. It will be understood that many substitutions, changes and variations in the described embodiments, applications and details of the methods and components illustrated herein and of their operation can be made by those skilled in the art without departing from the spirit of this invention.

What is claimed is:

1. A tampon insertion device for inserting a tampon from a tampon applicator into a vaginal canal, the tampon applicator having a barrel containing a tampon and a plunger for expelling the tampon from the distal end of the barrel, said device comprising:
    (a) a hollow casing having an open distal end, a proximal end, a top wall extending between the proximal and distal ends, an open bottom opposing said top wall, and a clamp portion located at the distal end of the casing;
    (b) a plunger actuator located in the interior of said casing for linear movement therein; and
    (c) a handle slidably positioned external to said casing and connected to said actuator such that linear sliding movement of said handle with respect to said casing causes a corresponding linear movement of said actuator within the casing;
wherein the interior of the casing is adapted to receive the tampon applicator plunger and a portion of the tampon applicator barrel therein, through the open bottom of the casing, with said clamp portion retaining the tampon applicator barrel such that the distal end of the barrel is spaced away from the distal end of, and external to, said casing with a proximal end of the plunger adjacent said actuator, such that linear movement of said handle in the direction of said distal end of the casing causes the tampon to be expelled from the distal end of the tampon applicator barrel while retaining the applicator barrel in said clamp portion.

2. The tampon insertion device of claim 1, wherein said actuator and said handle are linearly movable along an actuation plane that includes the centerline of the casing in order to expel a tampon from an applicator barrel secured within the clamp.

3. The tampon insertion device of claim 2, further comprising an enlarged flange portion extending laterally away from the distal end of said casing.

4. The tampon insertion device of claim 3, wherein said flange portion has a distal face that is orthogonal to said actuation plane, and a proximal face opposite the distal face.

5. The tampon insertion device of claim 2, wherein the top of said casing defines a linear rail having a void therethrough, said handle connected to said actuator through said void, wherein said handle is configured to slide along said linear rail.

6. The tampon insertion device of claim 2, wherein said handle is loop-shaped such that the user can insert her hand into the loop-shaped handle for manipulating the device.

7. The tampon insertion device of claim 2, wherein said clamp portion is configured to snap around a portion of the applicator barrel so as to retain the applicator barrel therein.

8. The tampon insertion device of claim 7, wherein said clamp portion is U-shaped.

9. The tampon insertion device of claim 1, wherein said clamp portion is configured to snap around a portion of the applicator barrel so as to retain the applicator barrel therein.

10. The tampon insertion device of claim 9, wherein said clamp portion is U-shaped.

11. A method of inserting a tampon into a user's vaginal canal, comprising the steps of:
(a) providing a tampon-loaded tampon insertion assembly having
a hollow casing having an open distal end, a proximal end, a top wall extending between the proximal and distal ends, and an open bottom opposing said top,
a plunger positioned within the hollow casing,
a barrel having an opening in its distal end through which a tampon can be expelled, a proximal portion of the barrel secured to or within the hollow casing such that a distal portion of the barrel extends distally away from, and external to, the hollow casing,
a handle slidably positioned external to the casing, and configured such that linear sliding movement of the handle with respect to the casing causes a corresponding linear movement of the plunger within the casing, and
a tampon positioned within the barrel;
(b) inserting the distal portion of the barrel into the vaginal canal; and
(c) sliding the handle of the insertion device distally with respect to the casing and towards the vagina such that the plunger expels the tampon from the opening in the distal end of the barrel and into the vaginal canal.

12. The method of claim 11, wherein the insertion assembly further comprises a plunger actuator located in the interior of the casing for linear movement therein, and further wherein the handle of the assembly is connected to the actuator such that, when the handle is slid distally with respect to the casing and towards the vagina, the actuator slides distally so as to urge the plunger distally and expel the tampon from the barrel and into the vaginal canal.

13. The method of claim 12, wherein the insertion assembly further comprises a clamp portion located at the distal end of the casing, and said step of providing a tampon-loaded tampon insertion assembly comprises:
providing an unloaded tampon insertion device having said hollow casing, slidable handle and plunger actuator connected to said slidable handle;
providing a tampon applicator assembly having said barrel containing the tampon and the plunger extending proximally away from the barrel; and
urging the tampon applicator assembly into the hollow casing such that the clamp portion snaps around the proximal portion of the barrel so as to retain the applicator barrel therein, with the proximal end of the plunger positioned adjacent the plunger actuator.

14. The method of claim 13, wherein tampon insertion device further includes an enlarged flange portion extending laterally away from the distal end of the casing, and further wherein the step of inserting the distal portion of the barrel into the vaginal canal comprises inserting the distal portion of the barrel is inserted into the vaginal canal until the enlarged flange portion prevents further penetration of the vaginal canal.

15. The method of claim 14, wherein the step of sliding the handle of the insertion device distally with respect to the casing and towards the vagina comprises urging the handle towards the vagina against the normal force provided by the contact between the enlarged flange portion and the user's body.

16. The method of claim 15, further comprising the step of the user inserting her hand into the handle prior to inserting the distal portion of the barrel into the vaginal canal.

17. The method of claim 16, wherein said step of sliding the handle of the insertion device distally with respect to the casing and towards the vagina comprises the user moving her arm towards her vagina.

\* \* \* \* \*